United States Patent
Schatz

[19]

[11] Patent Number: 5,902,332
[45] Date of Patent: May 11, 1999

[54] EXPANDABLE INTRALUMINAL GRAFT

[75] Inventor: Richard A. Schatz, Paradise Valley, Ariz.

[73] Assignee: Expandable Grafts Partnership, San Antonio, Tex.

[21] Appl. No.: 07/980,667

[22] Filed: Nov. 24, 1992

Related U.S. Application Data

[63] Continuation of application No. 07/657,296, Feb. 19, 1991, Pat. No. 5,195,984, which is a continuation of application No. 07/253,115, Oct. 4, 1988, abandoned.

[51] Int. Cl.⁶ .................................................. A61F 2/06
[52] U.S. Cl. .................................. 623/1; 623/12; 606/195
[58] Field of Search .................................. 623/1, 11, 12; 606/194, 195, 198

[56] References Cited

U.S. PATENT DOCUMENTS

| | | | |
|---|---|---|---|
| 861,659 | 7/1907 | Johnston . | |
| 3,599,641 | 8/1971 | Sheridan | 128/348 |
| 3,657,744 | 4/1972 | Ersek | 623/11 |
| 3,744,596 | 7/1973 | Sander | 188/203 |
| 3,968,800 | 7/1976 | Vilasi | 128/343 |
| 4,076,285 | 2/1978 | Martinez | 285/332 |
| 4,299,226 | 11/1981 | Banka | 128/344 |
| 4,300,244 | 11/1981 | Bokros | 128/334 |
| 4,323,071 | 4/1982 | Simpson et al. | 128/343 |
| 4,390,599 | 6/1983 | Broyles | 428/597 |
| 4,505,569 | 3/1985 | Dotter | 128/303 |
| 4,512,338 | 4/1985 | Balko et al. | 128/341 |
| 4,550,447 | 11/1985 | Seller, Jr. et al. | 128/334 |
| 4,553,545 | 11/1985 | Maass et al. | 128/341 |
| 4,560,374 | 12/1985 | Hanunerslag | 128/344 |
| 4,562,596 | 1/1986 | Kornberg | 128/334 |
| 4,580,568 | 4/1986 | Gianturco | 128/345 |
| 4,655,771 | 4/1987 | Wallsten | 128/343 |
| 4,676,341 | 6/1987 | Webb et al. | 128/207 |
| 4,731,054 | 3/1988 | Billeter et al. | 604/93 |
| 4,733,665 | 3/1988 | Palmaz | 128/343 |
| 4,739,762 | 4/1988 | Palmaz | 128/343 |
| 4,760,849 | 8/1988 | Kropf | 128/341 |
| 4,776,337 | 10/1988 | Palmaz | 128/343 |
| 4,787,899 | 11/1988 | Lazarus | 128/331 |
| 4,800,882 | 1/1989 | Gianburco | 128/343 |
| 4,856,516 | 8/1989 | Hillstead | 623/1 |
| 4,969,458 | 11/1990 | Wiktor | 606/194 |
| 4,998,923 | 3/1991 | Samson et al. | 606/194 |
| 5,102,417 | 4/1992 | Palmaz | 623/11 |
| 5,133,732 | 7/1992 | Wiktor | 623/1 |
| 5,135,536 | 8/1992 | Hillstead | 623/1 |

FOREIGN PATENT DOCUMENTS

| | | |
|---|---|---|
| 0 183 372 | 10/1983 | European Pat. Off. . |
| 0 145 166 | 10/1984 | European Pat. Off. . |
| 1 177 330 | 10/1985 | European Pat. Off. . |
| 0 221 570 | 11/1986 | European Pat. Off. . |
| 0421729 | 4/1991 | European Pat. Off. ................ 623/11 |
| 660689 | 11/1977 | U.S.S.R. . |
| 1457921 | 2/1989 | U.S.S.R. ................................. 623/1 |
| 1 205 743 | 10/1967 | United Kingdom . |
| 2 135 585 | 4/1983 | United Kingdom . |

OTHER PUBLICATIONS

J.E. Gordon, *Structures: or, Why Things Don't Fall Down*, Penguin Books, 1978, pp. 45 59, 132–148, 210–244, 377–383.

Maass et al., *Radiological Follow–up of Transluminally Inserted Vascular Endoprostheses: An Experimental Study Using Expanding Spirals*. Radiology 1984: 152:659–663.

(List continued on next page.)

*Primary Examiner*—Debra S. Brittingham
*Attorney, Agent, or Firm*—Tobor & Goldstein, L.L.P.

[57] ABSTRACT

A plurality of expandable and deformable intraluminal vascular grafts are expanded within a blood vessel by an angioplasty balloon associated with a catheter to dilate and expand the lumen of a blood vessel. The grafts may be thin-walled tubular members having a plurality of slots disposed substantially parallel to the longitudinal axis of the tubular members, and adjacent grafts are flexibly connected by a single connector member disposed substantially parallel to the longitudinal axis of the tubular members.

30 Claims, 3 Drawing Sheets

OTHER PUBLICATIONS

Wright et al., *Percutaneous Endovascular Stents: An Experimental Evaluation.* Radiology 1985;156:69–72.

Papanlcolaou et al., *Insertion of a Biliary Endoprosthesis Using a Balloon Dilation Catheter,* Gastrointest Radiol 10:394–396 (1985).

Palmaz et al., *Expandable Intraluminal Graft: A Preliminary Study,* Radiology 1985: 156:73–77.

Wallace et al., *Tacheobronchial Tree: Expandable Metallic Stents Used in Experimental and Clinical Applications.* Radiology 1986: 158:309–312.

Palmaz et al., *Expandable Intraluminal Vascular Graft: A Feasibility Study,* Surgery 1986: vol. 99 No. 2:199–205.

Palmaz et al., *Atherosclerotic Rabbit Aortas: Expandable Intraluminal Grafting,* Radiology 1986: 168:724–726.

Charnsangavej et al., *Stenosis of the Vena Cava: Preliminary Assessment of Treatment with Expandable Metallic Stents.* Radiology 1986: 161:295–298.

Duprat et al., *Flexible Balloon–expanded Stent for Small Vessels,* Radiology 1987; 162:276–278.

Rösch et al., *Experimental Intrahepatic Portacaval Anastomosis: Use of Expandable Gianturco Stents,* Radiology 1987; 162:481–485.

Palmaz, *The Current Status of Vascular Prostheses;* Rösch et al., *Gianturco Expandable Stents in Experimental and Clinical Use,* SCIVR 1987; 118–124.

Rösch et al., *Abstract: Modified Gianturco Expandable Wire Stents in Experimental and Clinical Use,* CIRSE, Porto Cervo, Sardinia, May 25–29, 1987.

Lawrence et al., *Percutaneous Endovascular Graft: Experimental Evaluation,* Radiology 1987; 163:357–360.

Palmaz et al., *Normal and Stenotic Renal Arteries: Experimental Balloon–expandable Intraluminal Stenting,* Radiology 1987; 164:705–708.

Rösch et al., *Glanturco Expandable Wire Stents in the Treatment of Superior Vena Cava Syndrome Recurring After Maximum–Tolerance Radiation,* Cancer 1987; 60:1243–1246.

Fallone et al., *Elastic Characteristics of the Self–expanding Metallic Stents,* Invest. Radiology 1988; 23:370–376.

Mullins et al., *Implantation of Balloon–expandable Intravascular Grafts by Catheterization in Pulmonary Arteries and Systemic Veins,* Circulation 77, No. 1, 186–189, 1988.

Yoshioka et al., *Self–Expanding Endovascular Graft: An Experimental Study in Dogs.* AJR:151, Oct. 1988; 673–676.

Mirich et al., *Percutaneously Placed Endovascular Grafts for Aortic Aneurysms: Feasibility Study,* Radiology 1989; 170:1033–1037.

Doller, *Transluminally–placed Coilspring Endarterial Tube Grafts,* Investigative Radiology, vol. 4, Sep.–Oct., 1969; 329–332.

Palmaz et al., *Abstract: Expandable Intraluminal Graft: A Preliminary Study,* Radiology, vol. 153(P), Nov. 1983; 70th Scientific Assembly and Annual Meeting.

Cragg et al., *Nonsurgical Placement of Arterial Endoprostheses: A New Technique Using Nitinol Wire,* Radiology 147:261–263, Apr. 1983.

J. Rösch et al., *Modified Gianturco Expandable Wire Stents In Experimental And Clinical Use,* Ann Radiol, vol. 31, No. 2, pp. 100–103 (1987).

J. Rösch et al., *Gianturco Expandable Stents In Experimental And Clinical Use,* Program: "Twelfth Annual Course On Diagnostic Angiography And Interventional Radiology" (Society of Cardiovascular and Interventional Radiology. Pittsburgh, PA) Mar. 23–26, 1987 (the "*Second Monofilament Article*").

J. Rösch et al., Abstract, *Expandable Gianturco–Type Wire Stents In Experimental Intrahepatic Portacaval Shunts,* Program: "72nd Scientific Assembly And Annual Meeting Of The Radiological Society Of North America". Nov. 30–Dec. 5, 1986, 161(P) Radiology 40, 41 (Nov., 1986) ("*The Monofilament Abstract*").

Wright et al., *Percutaneous Endovascular Stent: An Experimental Study* (Abstract), RSNA Meeting (Nov. 28, 1984).

Charnsangavej et al., *A New Expandable Metallic Stent For dilation of Stenotic Tubular Structures: Expandable and Clinical Evaluation,* Houston Medical Journal vol. 3, Jun. 1987, pp. 41–51.

Uchida et al., *Modifications of Gianturco Expandable Wire Stents,* AJR 1988, 150:1185–87.

Palmaz, *Balloon–Expandable Intravascular Stent,* AJR, 150:1263–69.

*Cordis Corporation v. Advanced Cardiovascular Systems, Inc., Guidant Corporation, Arterial Vascular Engineering, Inc., Boston Scientific Corporation and SCIMED Life Systems, Ino.,* Plantiff's Complaint, Oct. 23, 1997 (Case No. 97–550–SLR).

*Cordis Corporation v. Advanced Cardiovascular Systems, Inc., Guidant Corporation, Arterial Vasoular Engineering, Inc., Boston Scientific Corporation and SCIMED Life Systems, Inc.,* Defendants' Answer, Nov. 12, 1997 (Case No. 97–550–SLR).

*Cordis Corporation and Expandable Grafts Partnership v. Advanced Cardiovascular Systems, Inc., Guidant Corporation, Arterial Vascular Engineering, Inc., Boston Scientific Corporation and SCIMED Life Systems, Inc.,* Answer and Counterclaims of Defendant Advanced Cardiovascular Systems, Inc., Apr. 8, 1998 (Case No. 97–550–SLR).

*Arterial Vascular Engineering, Inc. v. Cordis Corporation, Johnson & Johnson and Expandable Grafts Partnership,* Plaintiff's First Amended Complaint for Declaratory Relief of Patent Validity, Unenforceability, Noninfringement, and for Antitrust Violations, Jan. 27, 1998 (Civil Action No. 97–700).

*Arterial Vascular Engineering, Inc. v. Cordis Corporation, Johnson & Johnson and Expandable Grafts Partnership,* Cordis Corporation and Johnson & Johnson's Answer and Counterclaim, Dec. 27, 1997 (Civil Action No. 97–700–SLR).

*Arterial Vascular Engineering, Inc. v. Cordis Corporation, Johnson & Johnson and Expandable Grafts Partnership,* Expandable Grafts Partnership's Answer, Feb. 27, 1998 (Civil Action No. 97–700–SLR).

*Arterial Vascular Engineering, Inc. v. Cordis Corporation, Johnson & Johnson and Expandable Grafts Partnership,* Reply of Plaintiff Arterial Vascular Engineering, Inc. to Counterclaims of Defendant Cordis Corporation, Mar. 31, 1997 (Civil Action No. 97–700–SLR).

*Arterial Vascular Engineering, Inc. v. Cordis Corporation, Johnson & Johnson and Expandable Grafts Partnership,* Reply of Plaintiff Arterial Vascular Engineering, Inc. to Counterclaims of Defendant Expandable Grafts Partnership, Mar. 31, 1997 (Civil Action No. 97–700–SLR).

*Cordis Corporation v. Advanced Cardiovascular Systems, Inc. and Guidant Corporation,* Cordis Corporation's Motion for a Preliminary Injunction, Oct. 8, 1997 (Civil Action No. 97–550).

*Cordis Corporation v. Advanced Cardiovascular Systems, Inc., Guidant Corporation, Arterial Vascular Engineering, Inc., Boston Scientific Corporation and SCIMED, Inc.,* Cordis's Motion for a Preliminary Injunction Against Arterial Vascular Engineering, Inc., Dec. 29, 1997 (Case No. 97–550–SLR).

Deposition of Richard Alan Schatz, M.D. in *Cordis Corporation v. Advanced Cardiovascular Systems, Inc.,* taken on Jan. 8, 1998 (Civil Action No. 97–550–SLR).

Deposition of Lee P. Bendel in *Cordis Corporation v. Advanced Cardiovascular Systems, Inc.,* taken on Jan. 22, 1998 (Civil Action No. 97–550–SLR).

Deposition of Julio Cesar Palmaz in *Cordis Corporation v. Advanced Cardiovascular Systems, Inc.,* taken on Dec. 29, 1997 (Civil Action No. 97–550–SLR).

Deposition of Richard A. Bowman in *Cordis Corporation v. Advanced Cardiovascular Systems, Inc.,* taken on Jan. 9, 1998 (Civil Action No. 97–550–SLR).

Deposition of Gary Schneiderman in *Cordis Corporation v. Advanced Cardiovascular Systems, Inc.,* taken on Jan. 16, 1998 (Civil Action No. 97–550–SLR).

Deposition of Richard Schatz, M.D. in *Cordis Corporation v. Advanced Cardiovascular Systems, Inc.,* taken on Jul. 14, 1998 (Civil Action No. 97–550–SLR).

Deposition of David Pearle, M.D. in *Cordis Corporation v. Advanced Cardiovascular Systems, Inc.,* taken on Jul. 10, 1998 (Civil Action No. 97–550–SLR).

Preliminary Injunction hearing testimony taken on Feb. 9–13, 1998 (Civil Action No. 97–550–SLR).

*Cordis Corporation v. Advanced Cardiovascular Systems, Inc. et al.* (Civil Action No. 97–550–SLR) and *Cordis Corporation v. Advanced Cardiovascular Systems, Inc. et al.* (Civil Action No. 98–65–SLR), Opening Post–Hearing Brief of Plaintiff Cordis Corporation in Support of Motion For a Preliminary Injunction, Mar. 6, 1998 (Portions relevant to patent claim construction and patent validity issues.).

*Cordis Corporation and Expandable Grafts Partnership v. Advanced Cardiovascular Systems, Inc., et al,* Post–Hearing Reply Brief of Plaintiff Cordis Corporation in Support of Its Motion for a Preliminary Injunction, Apr. 10, 1998 (Case No. 97–550–SLR) (Portions relevant to patent validity issues.).

*Cordis Corporation and Expandable Grafts Partnership v. Advanced Cardiovascular Systems, Inc., et al,* Plaintiffs' Motion for a Preliminary Injunction Against Boston Scientific Corporation and SCIMED Life Systems, Inc. and Memorandum in Support, Apr. 13, 1998 (Case No. 97–550–SLR).

*Cordis Corporation and Expandable Grafts Partnership v. Advanced Cardiovascular Systems, Inc., et al,* Judge Robinson's Order Denying Plaintiffs' Motion for a Preliminary Injunction, Jul. 17, 1998 (Civil Action No. 97–550–SLR).

*Cordis Corporation and Expandable Grafts Partnership v. Advanced Cardiovascular Systems, Inc., et al,* Defendants ACS and Guidant's Motion For Summary Judgment, Aug. 27, 1998 (Civil Action No. 97–550–SLR).

*Cordis Corporation and Expandable Grafts Partnership v. Advanced Cardiovascular Systems, Inc., et al,* Defendants Boston Scientific Corporation and SCIMED Life Systems, Inc.'s Motion For Summary Judgment of Invalidity of U.S. Patent No. 5,102,417, Aug. 27, 1998 (Civil Action No. 97–550–SLR).

*Cordis Corporation and Expandable Grafts Partnership v. Advanced Cardiovascular Systems, Inc., et al,* Plaintiffs' Answering Brief In Opposition To ACS's and BSC's Motion For Summary Judgment On Obviousness (Civil Action No. 97–550–SLR).

*Boston Scientific Limited et al. v. Expandable Grafts Partnership,* Plaintiffs' Statement of Claim, Mar. 13, 1997 (UK Action No. 1493).

*Boston Scientific Limited et al. v. Expandable Grafts Partnership,* Defendant's Amended Defence And Counterclaim, Aug. 14, 1997 (UK Action No. 1493).

*Boston Scientific Limited et al. v. Expandable Grafts Partnership,* Petition For Revocation, Mar. 13, 1997 (UK Action No. 1497).

*Boston Scientific Limited et al. v. Expandable Grafts Partnership,* Particulars Of Objections, Mar. 13, 1997 (UK Action No. 1497).

*Boston Scientific Limited et al. v. Expandable Grafts Partnership,* and *Boston Scientific Limited et al. v. Julio C. Palmaz,* Boston's Skeleton Argument (UK Action Nos. 1493, 1495, 1496 and 1497).

*Boston Scientific Limited et al. v. Julio C. Palmaz and Expandable Grafts Partnership,* Skeleton Argument of Palmaz/EGP, Mar. 19, 1998 (UK Action Nos. 1493, 1495, 1496 and 1497).

*Boston Scientific Limited et al. v. Expandable Grafts Partnership* and *Boston Scientific Limited et al. v. Julio C. Palmaz.* Boston's Closing Submissions (UK Action Nos. 1493, 1495, 1496 and 1497).

*Boston Scientific Limited et al. v. Julio C. Palmaz and Expandable Grafts Partnership,* EGP's Final Submissions, Apr. 2, 1998 (UK Action Nos. 1493, 1495, 1496 and 1497).

*Boston Scientific Limited et al. v. Julio C. Palmaz and Expandable Grafts Partnership,* Judgment, Jun. 26, 1998 (UK Action Nos. 1493, 1495, 1496 and 1497).

Rösch, *Modified Gianturco Expandable Wire Stents in Experimental and Clinical use,* CIRSE 1987 Presentation: see Witness Statement of Josef Rösch from U.K. Proceeding.

Statement of Claim by Boston Scientific et al. against Expandable Grafts Partnership et al. in *EPG et al. v. Boston Scientific et al.* in Netherlands (Mar. 13, 1997).

Motion For Joinder Of Actions, Change Of Claim and Statement Of Claim filed by Expandable Grafts Partnership et al. in *EPG et al. v. Boston Scientific et al.* in Netherlands (Apr. 22, 1997).

Opinion of K.J. Metman filed in *EPG et al. v. Boston Scientific et al.* in Netherlands (Aug. 29, 1997).

Expert Report of Dr. Nigel Buller in *EPG et al. v. Boston Scientific et al.* in Netherlands (Aug. 28, 1997).

Expert Report of Lee P. Bendel in *EPG et al. v. Boston Scientific et al.* in Netherlands (Aug. 28, 1997).

Memorandum Of Oral Pleading in *EPG et al. v. Boston Scientific et al.* in Netherlands (Sep. 12, 1997).

Plea Notes in *EPG et al. v. Boston Scientific et al.* in Netherlands (Sep. 12, 1997).

Provisional Judgment *EPG et al. v. Boston Scientific et al.* In Netherlands (Oct. 29, 1997).

Appeal filed by Expandable Grafts Partnership et al. in *EPG et al. v. Boston Scientific et al.* in Netherlands (Nov. 12, 1997).

Title filed by Boston Scientific et al. in *EPG et al. v. Boston Scientific et al.* in Netherlands (Jan. 22, 1998).

Statement of Rejoinder in the Action on the Merits, Also Including an Amendment of Defendants' Final Position in the Principal Action, as Well as the Provisional Statement of Rejoinder in the Action on the Counterclaim in *EPG et al. v. Boston Scientific et al.* in Netherlands (Feb. 10, 1998).

Statement of Answer in the Ancillary Appeal in *EPG et al. v. Boston Scientific et al.* In Netherlands (Feb. 19, 1998).

Plea Notes of P.A.M. Hendrick in *EPG et al. v. Boston Scientific et al.* in Netherlands (Mar. 10, 1998).

Decision of Court of Appeals in *EPG et al. v. Boston Scientific et al.* in Netherlands (Apr. 23, 1998).

Translation of Nullity Action Against EPO 0364 787 by Biotronik in Germany.

Translation of Nullity Action Against EPO 0 335 341 by Biotronik in Germany.

Translation of EPG Response to Nullity Action Against EP 0 364 787 by Biotronik in Germany.

Translation of EPG Response to Nullity Action Against EP 0 335 341 by Biotronik in Germany.

Nullity Suit Against EP–B1–0 335 341 Brought by Boston Scientific in Germany.

Translation of Opposition Filed by Terumo Corp. Against Japan Patent No. 2680901.

Translation of Decision on Opposition Against Japan Patent No. 2680901.

Translation of Judgment in Nullity Action Against EP 0 364 787 by Biotronik in Germany.

Translation of Judgment in Nullity Action Against EP 0 335 341 by Biotronik in Germany.

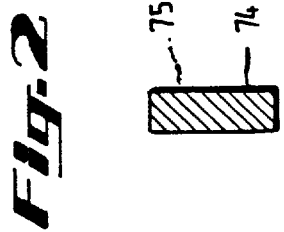
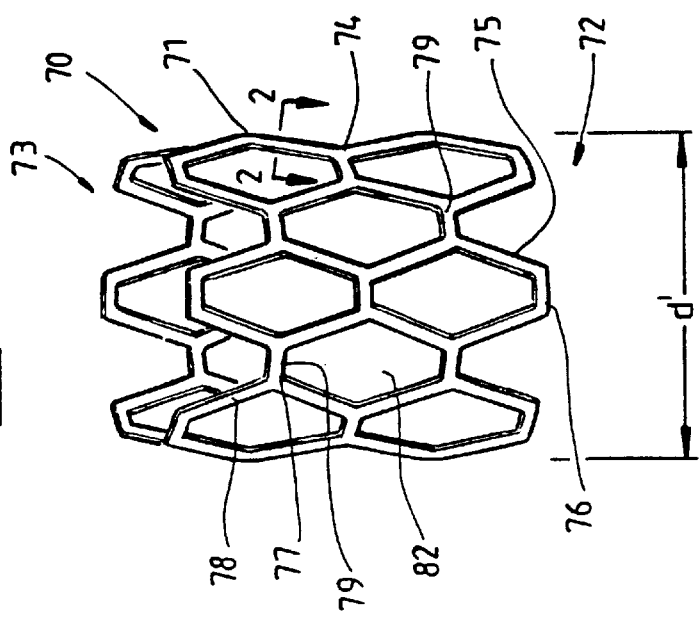
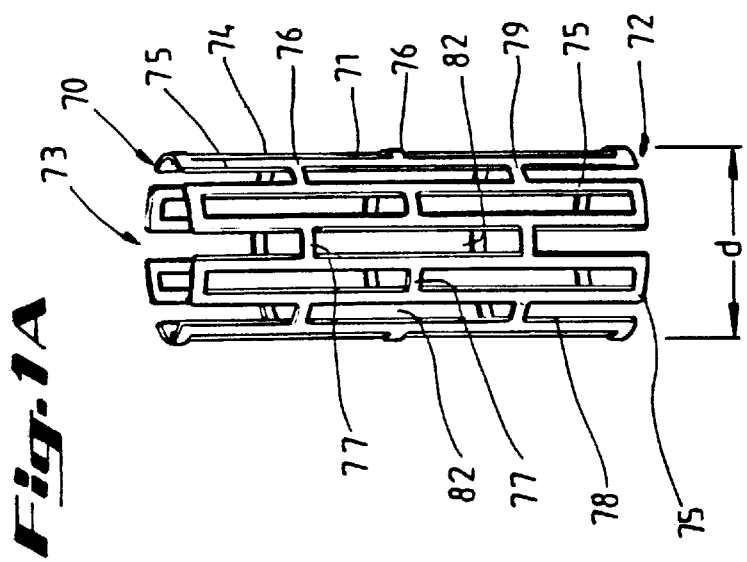

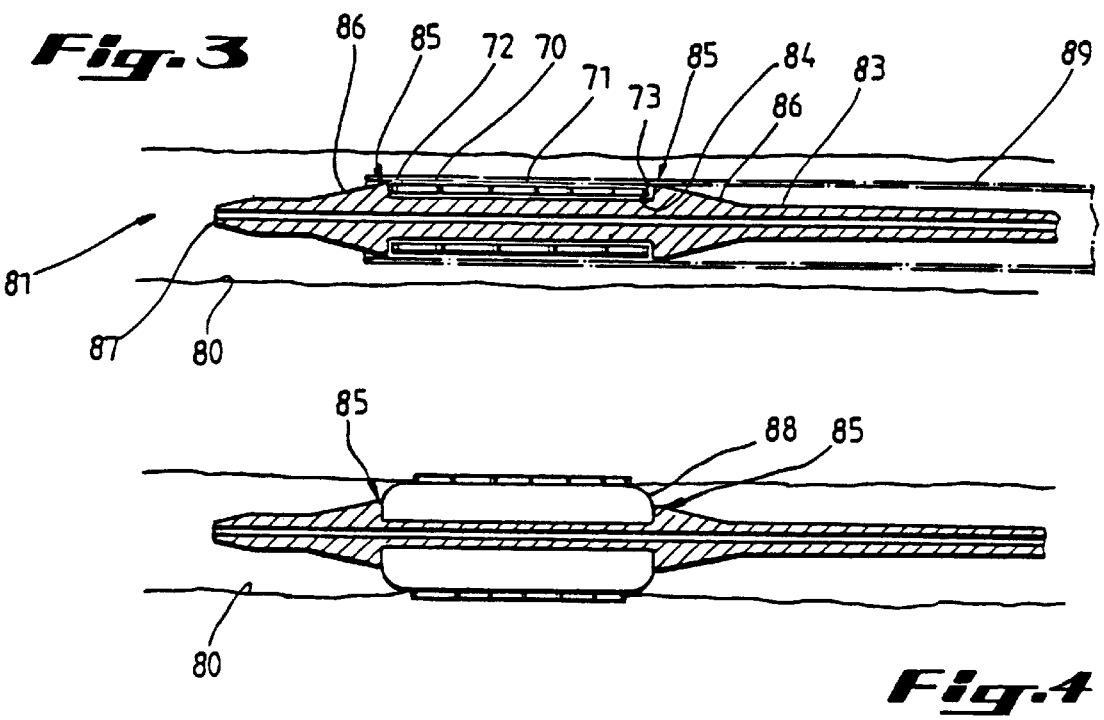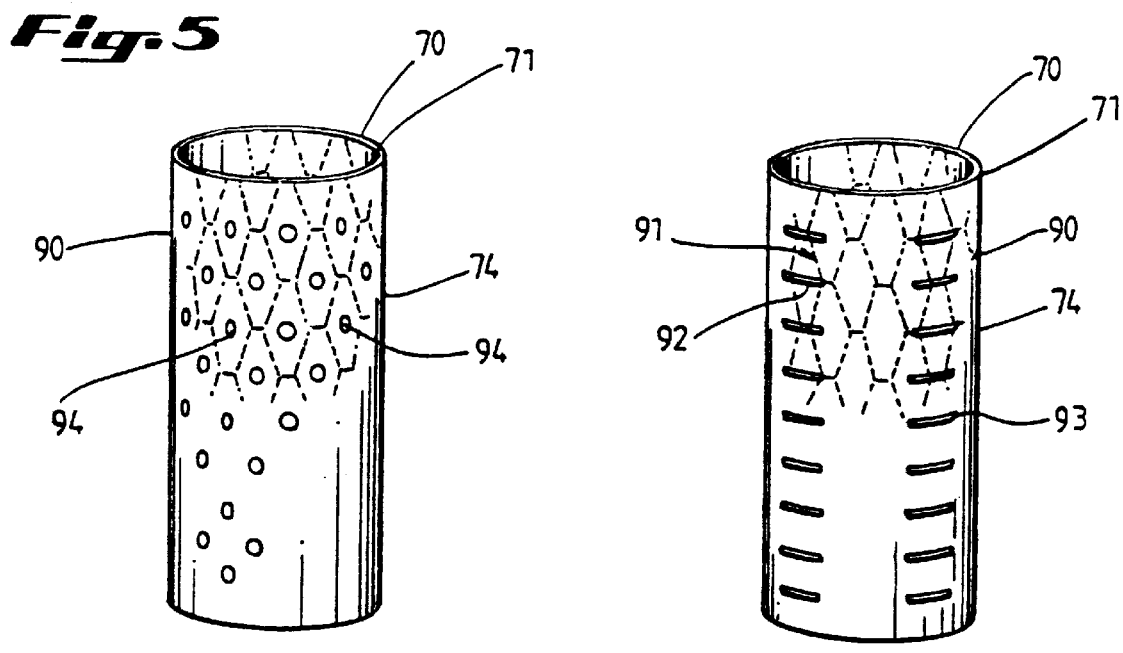

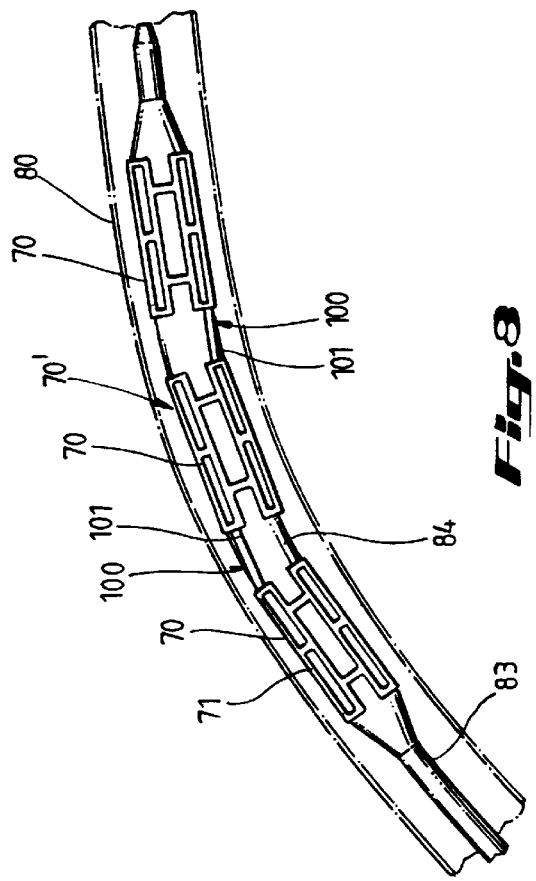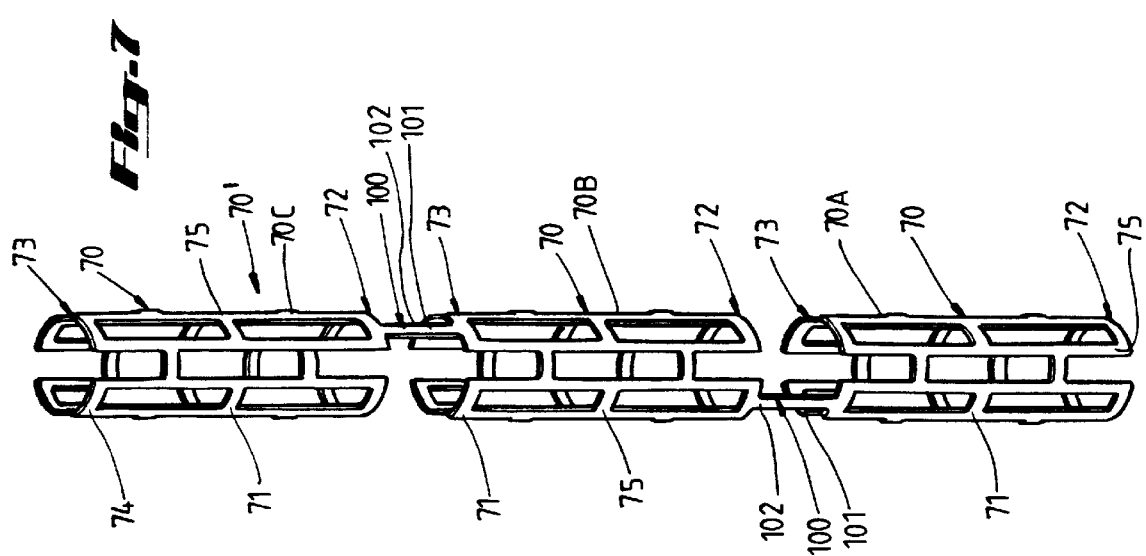

EXPANDABLE INTRALUMINAL GRAFT

This is a continuation, of application Ser. No. 07/657,296, filed Feb. 19, 1991, now U.S. Pat. No. 5,195,984, which is a continuation of application Ser. No. 07/253,115, filed Oct. 4, 1988, now abandoned.

FIELD OF THE INVENTION

The invention r elates to an expandable intraluminal graft for use within a body passageway or duct and, more particularly, expandable intraluminal vascular graft s which are particularly useful for repairing blood vessels narrowed or occluded by disease; and a method and apparatus for implanting expandable intraluminal grafts.

DESCRIPTION OF THE PRIOR ART

Intraluminal endovascular grafting has been demonstrated by experimentation to present a possible alternative to conventional vascular surgery. Intraluminal endovascular grafting involves the percutaneous insertion into a blood vessel of a tubular prosthetic graft and its delivery via a catheter to the desired location within the vascular system. Advantages of this method over conventional vascular surgery include obviating the need for surgically exposing, incising, removing, replacing, or bypassing the defective blood vessel.

Structures which have previously been used as intraluminal vascular grafts have included coiled stainless steel springs; helically wound coil springs manufactured from an expandable heat-sensitive material; and expanding stainless steel stents formed of stainless steel wire in a zig-zag pattern. In general, the foregoing structures have one major disadvantage in common. Insofar as these structures must be delivered to the desired location within a given body passageway in a collapsed state, in order to pass through the body passageway, there is no effective control over the final, expanded configuration of each structure. For example, the expansion of a particular coiled spring-type graft is predetermined by the spring constant and modulus of elasticity of the particular material utilized to manufacture the coiled spring structure. These same factors predetermine the amount of expansion of collapsed stents formed of stainless steel wire in a zig-zag pattern. In the case of intraluminal grafts, or prostheses, formed of a heat sensitive material which expands upon heating, the amount of expansion is likewise predetermined by the heat expansion characteristics of the particular alloy utilized in the manufacture of the intraluminal graft.

Thus, once the foregoing types of intraluminal grafts are expanded at the desired location within a body passageway, such as within an artery or vein, the expanded size of the graft cannot be changed. If the diameter of the desired body passageway has been miscalculated, an undersized graft might not expand enough to contact the interior surface of the body passageway, so as to be secured thereto. It may then migrate away from the desired location within the body passageway. Likewise, an oversized graft might expand to such an extent that the spring force, or expansion force, exerted by the graft upon the body passageway could cause rupturing of the body passageway. Further, the constant outwardly radiating force exerted upon the interior surface of the body passageway can cause erosion of the internal surface, or intima, of the artery or body passageway.

Another alternative to conventional vascular surgery has been percutaneous balloon dilation of elastic vascular stenoses, or blockages, through use of a catheter mounted angioplasty balloon. In this procedure, the angioplasty balloon is inflated within the stenosed vessel, or body passageway, in order to shear and disrupt the wall components of the vessel to obtain an enlarged lumen. With respect to arterial atheroscleerotic lesions, the relatively incompressible plaque remains unaltered, while the more elastic medial and adventitial layers of the body passageway stretch around the plaque. This process produces dissection, or a splitting and tearing, of the body passageway wall layers, wherein the intima, or internal surface of the artery or body passageway, suffers fissuring. This dissection forms a "flap" of underlying tissue which may reduce the blood flow through the lumen, or block the lumen. Typically, the distending intraluminal pressure within the body passageway can hold the disrupted layer or flap, in place. If the intimal flap created by the balloon dilation procedure is not maintained in place against the expanded intima, the intimal flap can fold down into the lumen and close off the lumen, or may even become detached and enter the body passageway. When the intimal flap closes off the body passageway, immediate surgery is necessary to correct this problem.

Although the balloon dilation procedure is typically conducted in the catheterization lab of a hospital, because of the foregoing problem, it is always necessary to have a surgeon on call should the intimal flap block the blood vessel or body passageway. Further, because of the possibility of the intimal flap tearing away from the blood vessel and blocking the lumen, balloon dilations cannot be performed upon certain critical body passageways, such as the left main coronary artery, which leads into the heart. If an intimal flap formed by a balloon dilation procedure abruptly comes down and closes off a critical body passageway, such as the left main coronary artery, the patient could die before any surgical procedures could be performed.

Additional disadvantages associated with balloon dilation of elastic vascular stenoses is that many fail because of elastic recoil of the stenotic lesion. This usually occurs due to a high fibrocollagenous content in the lesion and is sometimes due to certain mechanical characteristics of the area to be dilated. Thus, although the body passageway may initially be successfully expanded by a balloon dilation procedure, subsequent, early restenosis can occur due to the recoil of the body passageway wall which decreases the size of the previously expanded lumen of the body passageway. For example, stenoses of the renal artery at the ostium are known to be refractory to balloon dilation because the dilating forces are applied to the aortic wall rather than to the renal artery itself. Vascular stenoses caused by neointimal fibrosis, such as those seen in dialysis-access fistulas, have proved to be difficult to dilate, requiring high dilating pressures and larger balloon diameters. Similar difficulties have been observed in angioplasties of graft-artery anastomotic strictures and postendarterectomy recurrent stenoses. Percutaneous angioplasty of Takayasu arteritis and neurofibromatosis arterial stenoses may show poor initial response and recurrence which is believed due to the fibrotic nature of these lesions.

For repairing blood vessels narrowed or occluded by disease, or repairing other body passageways, the length of the body passageway which requires repair, as by the insertion of a tubular prosthetic graft, may present problems if the length of the required graft cannot negotiate the curves or bends of the body passageway through which the graft is passed by the catheter. In other words, in many instances, it is necessary to support a length of tissue within a body passageway by a graft, wherein the length of the required graft exceeds the length of a graft which can be readily delivered via a catheter to the desired location within the vascular system. Some grafts do not have the requisite ability to bend so as to negotiate the curves and bends present within the vascular system, particularly prostheses or grafts which are relatively rigid and resist bending with respect to their longitudinal axes.

Accordingly, prior to the development of the present invention, there has been no expandable intraluminal vascular graft for expanding the lumen of a body passageway, which: prevents recurrence of stenoses in the body passageway; can be utilized for critical body passageways, such as the left main coronary artery of a patient's heart; prevents recoil of the body passageway wall; allows the intraluminal graft to be expanded to a variable size to prevent migration of the graft away from the desired location and prevents rupturing and/or erosion of the body passageway by the expanded graft; permits tissue of an elongated section of a body passageway to be supported by an elongated graft; and provides the necessary flexibility to negotiate the bends and curves in the vascular system. Therefore, the art has sought an expandable intraluminal vascular graft which: prevents recurrence of stenoses in the body passageway; is believed to be able to be utilized in critical body passageways, such as the left main coronary artery of the heart; prevents recoil of the body passageway; can be expanded to a variable size within the body passageway to prevent migration of the graft away from the desired location and to prevent rupturing and/or erosion of the body passageway by the expanded graft; permits tissue of an elongated section of a body passageway to be supported by an elongated graft; and provides the necessary flexibility to negotiate the bends and curves in the vascular system.

SUMMARY OF THE INVENTION

In accordance with the invention, the foregoing advantages have been achieved by the present expandable intraluminal vascular graft. The present invention includes a plurality of thin-walled tubular members, each having first and second ends and a wall surface disposed between the first and second ends, the wall surface having a substantially uniform thickness and a plurality of slots formed therein, the slots being disposed substantially parallel to the longitudinal axis of each tubular member; a single connector member being disposed between adjacent tubular members to flexibly connect adjacent tubular members, the single connector member being disposed in a substantially parallel relationship with respect to the longitudinal axis of the tubular members and coplanar with each tubular member; each tubular member having a first diameter which permits intraluminal delivery of the tubular members into a body passageway having a lumen; and the tubular members having a second, expanded and deformed diameter, upon the application from the interior of the tubular members of a radially, outwardly extending force, which second diameter is variable and dependent upon the amount of force applied to the tubular members, whereby the tubular members may be expanded and deformed to expand the lumen of the body passageway.

A further feature of the present invention is that the single connector member may be a thin-walled, elongate bar member, coplanar with adjacent tubular members. An additional feature of the present invention is that a first connector member may be disposed between the second end of a first tubular member and the first end of a second tubular member; a second connector member may be disposed between the second end of the second tubular member and the first end of a third tubular member; the first and second connector members being angularly offset from one another with respect to the longitudinal axis of the tubular members.

The expandable intraluminal vascular graft of the present invention, when compared with previously proposed prior art intraluminal grafts, has the advantages of: preventing recurrence of stenoses; is believed to permit implantation of grafts in critical body passageways, such as in the left main coronary artery of the heart; prevents recoil of the body passageway; prevents erosion of the body passageway by the expanded graft; permits expansion of the graft to a variable size dependent upon conditions within the body passageway; permits tissue of an elongated section of a body passageway to be supported by an elongated graft; and provides the necessary flexibility to negotiate the bends and curves in tortuous body passageways, such as the vascular system.

BRIEF DESCRIPTION OF THE DRAWINGS:

In the drawings:

FIG. 1A is a perspective view of an expandable intraluriinal vascular graft, or prosthesis for a body passageway, having a first diameter which permits delivery of the graft, or prosthesis, into a body passageway;

FIG. 1B is a perspective view of the graft, or prosthesis, of FIG. 1A, in its expanded configuration when disposed within a body passageway;

FIG. 2 is a cross-sectional view of the prosthesis taken along line 2—2 of FIG. 1B;

FIG. 3 is a cross-sectional view of an apparatus for intraluminally reinforcing a body passageway, or for expanding the lumen of a body passageway, illustrating a prosthesis, or intraluminal vascular graft, in the configuration shown in FIG. 1A;

FIG. 4 is a cross-sectional view of the apparatus for intraluminally reinforcing a body passageway, or for expanding the lumen of a body passageway, with the graft, or prosthesis, in the configurations shown in FIG. 1B;

FIGS. 5 and 6 are perspective views of prostheses for a body passageway, with the grafts, or prostheses, having a coating thereon;

FIG. 7 is a perspective view of another embodiment of a graft or prosthesis in accordance with the present invention; and FIG. 8 is a perspective view of the graft of FIG. 7, wherein the graft has been bent or articulated.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF THE INVENTION

In FIGS. 1A and 1B, an expandable intraluminal vascular graft, or expandable prosthesis for a body passageway, 70 is illustrated. It should be understood that the terms "expandable intraluminal vascular graft" and "expandable prosthesis" are interchangeably used to some extent in describing the present invention, insofar as the methods, apparatus, and structures of the present invention may be utilized not only in connection with an expandable intraluminal vascular graft for expanding partially occluded segments of a blood vessel, or body passageway, but may also be utilized for many other purposes as an expandable prosthesis for many other types of body passageways. For example, expandable prostheses 70 may also be used for such purposes as: (1) supportive graft placement within blocked arteries opened by transluminal recanalization, but which are likely to collapse in the absence of an internal support; (2) similar use following catheter passage through mediastinal and other veins occluded by inoperable cancers; (3) reirforcement of catheter created intrahepatic communications between portal and hepatic veins in patients suffering from portal hypertension; (4) supportive graft placement of narrowing of the esophagus, the intestine, the ureters, the urethra; and (5) supportive graft reinforcement of reopened and previously obstructed bile ducts. Accordingly, use of the term "prosthesis" encompasses the foregoing usages within various types of body passageways, and the use of the term "intraluminal vascular graft" encompasses use for expanding the lumen of a body passageway. Further, in this regard, the term "body passageway" encompasses any duct within the human body, such as those previously described, as well as any vein, artery, or blood vessel within the human vascular system.

Still with reference to FIGS. 1A and 1B, the expandable intraluminal vascular graft, or prosthesis, 70 is shown to generally comprise a tubular member 71 having first and second ends 72, 73 and a wall surface 74 disposed between the first and second ends 72, 73. Tubular member 71 has a first diameter, d, which, to be hereinafter described in greater detail, permits intraluminal delivery of the tubular member 71 into a body passageway 80 having a lumen 81 (FIG. 3). With reference to FIG. 1B, upon the application from the interior of the tubular member 71 of a radially, outwardly extending force, to be hereinafter described in greater detail tubular member 71 has a second, expanded diameter, d', which second diameter d' is variable in size and dependent upon the amount of force applied to deform the tubular member 71.

Tubular member 71, may be any suitable material which is compatible with the human body and the bodily fluids (not shown) with which the vascular graft, or prosthesis, 70 may come into contact. Tubular member 71 must also be made of a material which has the requisite strength and elasticity characteristics to permit the tubular member 71 to be expanded and deformed from the configuration shown in FIG. 1A to the configuration shown illustrated in FIG. 1B and further to permit the tubular member 71 to retain its expanded and deformed configuration with the enlarged diameter d' shown in FIG. 1B and resist radial collapse. Suitable materials for the fabrication of tubular member 71 would include silver, tantalum, stainless steel, gold, titanium or any suitable plastic material having the requisite characteristics previously described.

Preferably, tubular member 71 is initially a thin-walled stainless steel tube having a uniform wall thickness;, and a plurality of slots 82 are formed in the wall surface 74 of tubular member 71. As seen in FIG. 1A Chen tubular member 71 has the first diameter d, the slots 82 are disposed substantially parallel to the longitudinal axis of the tubular member 71. As seen in FIG. 1A, the slots 82 are preferably uniformly and circumferentially spaced from adjacent slots 82, as by connecting members 77, which connecting members 77 preferably have a length equal to the width of slots 82, as seen in FIG. 1A. Slots 82 are further uniformly spaced from adjacent slots 82 along the longitudinal axis of the tubular member 71, which spacing is preferably equal to the width of connecting members 77. Thus, the formation of slots 82 results in at least one elongate member 75 being formed between adjacent slots 82, elongate member 75 extending between the first and second ends, 72, 73 of tubular member 71, as seen in FIG. 1A.

Still with reference to FIG. 1A, each slot will have first and second ends with a connecting member 77 disposed at the first and second ends of slots 82. Preferably, the first and second ends of each slot 82 are disposed intermediate the first and second ends of adjacent slots 82 along the longitudinal axis of the tubular member 71. Thus, connecting members 77, which are disposed at the first and second ends of each slot 82, and between elongate members 75, will in turn be disposed intermediate the first and second ends of adjacent slots 82 along the longitudinal axis of the tubular member 71. Accordingly, slots 82 are preferably uniformly and circumferentially spaced from adjacent slots, and slots 82 adjacent to one another along the longitudinal axis of tubular member 71 are in a staggered relationship with one another. Alternating slots disposed about the circumference of tubular member 71 at both the first and second ends 72, 73 of tubular member 71 will only have a length equal to approximately one-half of the length of a complete slot 82, such half-slot 82 being bounded by members 78, 79, at both the first and second ends 72, 73 of tubular member 71. Although the graft, or prosthesis, 70 of FIGS. 1A and 1B is illustrated to have a length approximately equal to the length of two slots 82, it should be apparent that the length of the graft 70 could be made longer or shorter as desired.

The foregoing described construction of graft, or prosthesis, 70 permits graft, or prosthesis, 70 to be expanded uniformly, and outwardly, in a controlled manner into the configuration shown in FIG. 1B, upon the application of a suitable force from the interior of tubular member 71, as will be hereinafter described in greater detail. The expansion of tubular member 71 into the configuration shown in FIG. 1B is further uniform along the length of tubular member 71, not only because of the uniform spacing between slots 82, as previously described, but also because the thickness of the wall surface 74, or the thickness of connecting members 77, elongate members 75, and members 78, 79, is the same uniform thickness. As illustrated in FIG. 2, the uniform thickness of elongate member 75 is shown, and the preferred cross-sectional configuration of elongate member 75, connecting member 77, and members 78, 79, is illustrated, which configuration is rectangular. It should of course be understood by those skilled in the art, that the cross-sectional configuration of the foregoing components of graft, or prosthesis, 70 could also be square, rectangular, or other cross-sectional configurations. As will be hereinafter described in greater detail, it is preferable that the outer surface 74 of graft, or prothesis, 70, which would be in contact with the body passageway 80 FIG. 4, should be relatively smooth.

With reference to FIG. 1B, it is seen that after the graft, or prosthesis 70, has been expanded and deformed into the configuration of FIG. 1B, the slots 82 will assume a substantially hexagonal configuration when the tubular member 71 has the second, expanded diameter, d', as shown in FIG. 1B. Such a hexagonal configuration will result when the slots 82 initially have a substantially rectangular configuration when the tubular member 71 has the first diameter, d, illustrated in FIG. 1A. It should be noted that were the width of slots 82 to be substantially reduced, whereby the length of connecting member 77 would approximate a single point intersection, the expansion of such a tubular member 71 would result in slots 82 assuming a configuration which would be substantially a parallelogram (not shown).

It should be noted that not only is tubular member 71 expanded from the configuration shown in FIG. 1A to achieve the configuration shown in FIG. 1B, but tubular member 71 is further "deformed" to achieve that configuration. By use of the term "deformed" is meant that the material from which graft, or prosthesis, 70 is manufactured is subjected to a force which is greater than the elastic limit of the material utilized to make tubular member 71. Accordingly, the force is sufficient to permanently bend elongate members 75 whereby segments of the elongate members 75 pivot about connecting members 77 and move in a circumferential direction as they pivot, whereby the diameter of the tubular member 71 increases from the first diameter, d, to the expanded diameter, d', of FIG. 1B. The force to be applied to expand tubular member 71, which is applied in the manner which will be hereinafter described in greater detail, must thus be sufficient to not only expand tubular member 71, but also to deform elongate member 75, in the manner previously described, whereby the portions of the elongate members 75 which pivot about the ends of connecting members 77 do not "spring back" and assume their configuration shown in FIG. 1A, but rather retain the configuration thereof in FIG. 1B. Once graft, or prosthesis, 70 has been expanded and deformed into the configuration shown in FIG. 1B, graft, or prosthesis 70, will serve to prevent a body passageway from collapsing as will be hereinafter described in greater detail. It should be noted that when tubular member 71 has the first diameter, d, shown in FIG. 1A, or after tubular member 71 has been expanded and deformed into the second, expanded diameter, d', of FIG. 1B, tubular member 71 does not exert any outward, radial force, in that tubular member 71 is not a "spring-like" or "selfexpanding member", which would tend to exert an outwardly radial force.

With reference now to FIGS. 3 and 4, apparatus of the present invention will be described in greater detail. Once again, it should be understood that the apparatus of the present invention is useful not only for expanding the lumen of a body passageway, such as an artery, vein, or blood vessel of the human vascular system, but are also useful to perform the previously described procedures to intraluminally reinforce other body passageways or ducts, as previously described. Still with reference to FIGS. 3 and 4, an expandable intraluminal vascular graft, or prosthesis, 70, of the type described in connection with FIGS. 1A and 1B, is disposed or mounted upon a catheter 83. Catheter 83 has an expandable, inflatable portion 84 associated therewith. Catheter 83 may include means for mounting and retaining 85 the expandable intraluminal vascular graft, of prosthesis, 70 on the expandable, inflatable portion 84 of catheter 83. The mounting and retaining means 85 could comprise retainer ring members 86 disposed on the catheter 83 adjacent the expandable inflatable portion 84 of catheter 83; and a retainer ring member 86 is disposed adjacent each end 72, 73 of the expandable intraluminal vascular graft, or prosthesis, 70. As seen in FIG. 3, retainer ring members could be formed integral with catheter 83, and the retainer ring member 86 adjacent the leading tip 87 of catheter 83 slopes upwardly and away from catheter tip 87 in order to protect and retain graft or prosthesis, 70 as it is inserted into the lumen 81 of body passageway 80, as to be hereinafter described in greater detail. The remaining retainer ring member 86 as shown in FIG. 3, slopes downwardly away from tip 87 of catheter 83, to insure easy removal of catheter 83 from body passageway 80. After expandable intraluminal graft, or prosthesis, 70 has been disposed upon catheter 83, in the manner previously described, the graft, or prosthesis, 70 and catheter 83 are inserted within a body passageway 80 by catheterization of the body passageway 80 in a conventional manner.

In a conventional manner, the catheter 83 and graft, or prosthesis, 70 are delivered to the desired location within the body passageway 80, whereat it is desired to expand the lumen 81 of body passageway 80 via intraluminal graft 70, or where it is desired to implant prosthesis 70. Fluoroscopy, and/or other conventional techniques may be utilized to insure that the catheter 83 and graft, or prosthesis, 70 are delivered to the desired location within the body passageway. Prosthesis, or graft, 70 is then controllably expanded and deformed by controllably expanding the expandable, inflatable portion 84 of catheter 83, whereby the prosthesis, or graft, 70 is expanded and deformed radially, outwardly into contact with the body passageway 80, as shown in FIG. 4. In this regard, the expandable, inflatable portion of catheter 83 may be a conventional angioplasty balloon 88. After the desired expansion and deformation of prosthesis, or graft, 70 has been accomplished, angioplasty balloon 88 may be collapsed, or deflated, and the catheter 83 may be removed in a conventional manner from body passageway 80. If desired, as seen in FIG. 3, catheter 83, having graft or prosthesis, 70 disposed thereon, may be initially encased in a conventional Teflon sheath 89, or a sheath 89 made of another suitable material, which is pulled away from prosthesis, or graft, 70, prior to expansion of the prosthesis, or graft, 70.

Still with reference to FIGS. 3 and 4, it should be noted that tubular member 71 of prosthesis, or graft, 70 initially has the first predetermined, collapsed diameter, d, as described in connection with FIG. 1A, in order to permit the insertion of the tubular member, 71 into the body passageway 80 as previously described. When it is desired to implant prosthesis 70 within a body passageway 80 for the purposes previously described, the prosthesis 70 is, controllably expanded and deformed to the second diameter, d', and the second, expanded diameter, d', is variable and determined by the internal diameter of the body passageway 80, as shown in FIG. 4, and by the amount of expansion of the inflatable portion 84 of catheter 83. Accordingly, the expanded and deformed prosthesis 70, upon deflation of angioplasty balloon 88 will not be able to migrate from the desired location within the body passageway 80, nor will the expansion of the prosthesis 70 be likely to cause a rupture of the body passageway 80. Furthermore, insofar as prosthesis, or graft, 70 is not a "spring-like" or "self-expanding member", the prosthesis is not consistently applying an outward, radial force against the interior surface of body passageway 80, in excess of that required to resist radial collapse of the body passageway 80. Thus, erosion of the interior surface, or intima, of the artery or body passageway is prevented.

When it is desired to use expandable intraluminal graft 70 to expand the lumen 81 of a body passageway 80 having an area of stenosis, the expansion of intraluminal vascular graft 70 by angioplasty balloon 88, allows controlled dilation of the stenotic area and, at the same time controlled expansion and deformation of the vascular graft 70, whereby vascular graft 70 prevents the body passageway 80 from collapsing and decreasing the size of the previously expanded lumen 81. Once again, the second, expanded diameter d' of intraluminal vascular graft 70, as shown in FIG. 4, is variable and determined by the desired expanded internal diameter of body passageway 80. Thus, the expandable intraluminal graft 70 will not migrate away from the desired location within the body passageway 80 upon deflation of angioplasty balloon 88, nor will the expansion of intraluminal graft 70 likely cause a rupture of body passageway 80, nor any erosion as previously described. Further, should an intimal flap, or fissure, be formed in body passageway 80 at the location of graft 70, graft 70 will insure that such an intimal flap will not be able to fold inwardly into body passageway 80, nor tear loose and flow through body passageway 80. In the situation of utilizing graft 70 in the manner previously described to expand the lumen of a portion of a critical body passageway, such as the left main coronary artery, it is believed that the intimal flap will be unable to occlude the left main coronary artery of the heart and cause the death of the patient.

Because it is only necessary to inflate angioplasty balloon 88 one time in order to expand and deform graft 70, it is believed that a greater amount of endothelium, or inner layer of the intima, or inner surface of the body passageway, will be preserved, insofar as the extent of endothelial denudation during transluminal angioplasty is proportional to the balloon inflation time. Further, in theory, the amount of preserved endothelium should be large because in the expanded configuration of graft 70, potentially 80% of the endothelium is exposed through the openings or expanded slots 82 of graft 70. It is further believed that intact patches of endothelium within expanded slots 82 of graft 70 may result in a rapid, multicentric endothelialization pattern as shown by experimental studies.

With reference now to FIGS. 5 and 6, prostheses, or grafts, 70 of the type previously described in connection with FIGS. 1A and 1B are shown, and the tubular members 71 of grafts, or prostheses, 70 have a biologically inert or biologically compatible coating 90 placed upon wall surfaces 74 of tubular shaped members 71. Examples of a suitable biologically inert coating would be porous polyurethane, Teflon , or other conventional biologically inert plastic materials. The coating 90 should be thin and highly elastic so as not to interfere with the desired expansion and deformation of prosthesis, or graft, 70. Coating 90 may be further provided with a means for anchoring 91 (FIG. 6) the tubular member 71 to the body passageway 80. Anchoring means 91 may be comprised of a plurality of radially, outwardly extending projections 92 formed on the coating 90. As seen in FIG. 6, the radially outwardly extending projections 92 could comprise a plurality of ridges 93, or other types of radially, outwardly extending projections. Further, it may be desirable to have a plurality of openings 94 formed in coating 90, as shown in FIG. 5, whereby the fluid contained in body passageway 80 can be in direct contact with the dilated, or expanded, body passageway area. Examples of biologically compatible coatings 90 would include coatings made of absorbable polymers such as those used to manufacture absorbable sutures. Such absorbable polymers include polyglycoides, polylactides, and copolymers thereof. Such absorbable polymers could also contain various types of drugs, whereby as the coating 90 is absorbed, or dissolves, the drug would be slowly released into the body passageway 80.

Turning now to FIGS. 7 and 8, an expandable intraluminal vascular graft, or prosthesis, 70' is shown for implantation in curved body passageways 80, or for use in the elongated sections of body passageway 80, when a prosthesis or a graft, 70' is required which is longer than the graft, or prosthesis, 70 of FIG. 1A. Identical reference numerals are used throughout FIGS. 7 and 8 for elements which are the same in design, construction, and operation, as those previously described in connection with FIGS. 1A–6, and primed reference numerals are used for elements which are similar in construction, design, and operation, as those previously described in connection with 1A–6.

As seen in FIG. 7, graft, or prosthesis, 70' generally includes a plurality of prostheses, or grafts, 70 as described previously in connection with FIGS. 1A, 1B, and 2. Disposed between adjacent tubular members, 71, or adjacent grafts, or prostheses, 70, is a single connector member 100 to flexibly connect adjacent tubular members 71 or grafts, or prostheses, 70. Connector members 100 are preferably formed of the same material as grafts 70, as previously described, and connector members 100 may be formed integrally between adjacent grafts 70, or tubular members 71, as shown in FIG. 7. The cross-sectional configuration of connector members 100, along the longitudinal axis of graft, or prosthesis, 70', is the same, in that connector members 100 have the same uniform wall thickness of elongate members 75 and thus form a thin-walled, elongate bar member 101 which is coplanar with adjacent tubular members 71. Of course, it should be readily apparent to one of ordinary skill in the art, that the thickness of connector members 100 could alternatively be smaller than elongate member 75; however, it is preferable that the outer circumferential surface 102 of connector members 100 lies in the same plane formed by the wall surfaces 74 of grafts, or prostheses, 70, as seen in FIG. 7.

Still with reference to FIGS. 7–8, it should be noted that although graft, or prosthesis, 70' is illustrated as including three grafts, or prostheses, 70 flexibly connected to one another by connector members 100, as few as two grafts 70 could be connected to form graft, or prosthesis, 70'. Furthermore, many grafts 70 could be flexibly connected by connector members 100 as are desired to form graft, or prosthesis, 70'. Preferably, the length of each graft, or prosthesis, 70 is approximately the length of two slots 82; however, the length of each graft 70 could be approximately equal to the length of two or more slots 82. When three or more grafts 70 are flexibly connected by connector members 100, as shown in FIGS. 7 and 8, preferably a first connector member 100 is disposed between the second end 73 of a first tubular member 70A and the first end 72 of a second tubular member 70B. A second connector member 100 is then disposed between the second end 73 of the second tubular member 70B and the first end 72 of a third tubular member 70C. The first and second connector members 100, as shown in FIGS. 7 and 8, may be angularly offset from one another with respect to the longitudinal axis of the tubular members 70 to permit the requisite flexibility between the interconnected grafts, or prostheses, 70.

The delivery and expansion of graft, or prosthesis, 70' is the same as that previously described in connection with FIGS. 1A, 1B, and 3–4. The length of the expandable, inflatable portion 84 of catheter 83 would be sized to conform with the length of the graft, or prosthesis, 70', as should be readily apparent to one of ordinary skill in the art. Except for the length of the expandable, inflatable portion 84, catheter 83, the method of delivery of graft, or prosthesis, 70' and its subsequent, controllable expansion and deformation are the same as previously described. As seen in FIG. 8, the prosthesis 70' is illustrated in the configuration it would assume when being delivered to the desired location within the body passageway 80, and the graft, or prosthesis, 70' is disposed upon catheter 83 and is passing through a curved portion of body passageway 80, such as an arterial bend. Because of the disposition of flexible connector members 100 between adjacent tubular members 71, or grafts, or prostheses, 70, graft, or prosthesis, 70' is able to flexibly bend, or articulate, with respect to the longitudinal axis of graft, or prosthesis, 70', so as to be able to negotiate the curves or bends found in body passageways 80. It should be noted that connector members 100 permit the bending, or articulation of adjacent tubular members 71 in any direction about the longitudinal axis of graft, or prosthesis, 70'. When graft, or prosthesis, 70' is in its expanded, and deformed configuration, tubular members 71 of graft, or prosthesis, 70', will assume the configuration shown in FIG. 1B.

It is to be understood that the invention is not to be limited to the exact details of construction, operation, exact materials, or embodiments shown and described, as obvious modifications and equivalents will be apparent to one skilled in the art. Accordingly, the invention is therefore to be limited only by the scope of the appended claims.

I claim:

1. A balloon expandable coronary stent for delivery to a coronary artery through an access artery, the stent comprising:

at least three segments, each segment having a generally tubular shape and a fist end and a second end;

each segment having a plurality of openings that are disposed substantially parallel to the longitudinal axis of the segment, the openings forming a series of alternating open and closed portions in each of the first and second ends of the segment;

the segments being arranged so that at least one closed portion of the second end of a first segment is in longitudinal alignment with a closed portion of the first end of a second segment and at least one closed portion of the second end of the second segment is in longitudinal alignment with a closed portion of the first end of the third segment;

a first connector joining the aligned closed portion of the second end of the first segment to the aligned closed portion of the first end of the second segment;

a second connector joining the aligned closed portion of the second end of the second segment to the aligned closed portion of the first end of the third segment;

the first and second connectors being angularly offset from each other with respect to the longitudinal axis of the stent;

whereby each of the segments may be displaced at an angle with respect to the longitudinal axis of an adjacent segment when the stent is delivered through a cued portion of the access or coronary arteries; and the stent having a first diameter which permits intraluminal delivery of the stent through the access artery by percutaneous catheterization and a second, expanded and deformed diameter, the second diameter being attained upon the application from the interior of the stent of a radially, outwardly directed force by inflating a balloon, which second diameter is variable and dependent upon the amount of force applied to the stent, whereby the stent may be expanded and deformed beyond its elastic limit to expand the lumen of the coronary artery.

2. The stent of claim 1 wherein at least one of the first and second connectors is flexible.

3. The stent of claim 1 wherein the segments may articulate about the first and second connectors.

4. The stent of claim 1 wherein the first connector is located at and unified with the closed portion of the second end of the first segment and the closed portion of the first end of the second segment and the second connector is located at and unified with the closed portion of the second end of the second segment and the closed portion of the first end of the third segment.

5. The stent of claim 1 wherein each of the segments include at least one cylindrical element formed from a plurality of struts so as to define the open and closed portions.

6. The stent of claim 1 wherein at least one of the segments may individually function as a structure for maintaining patency of the lumen of the coronary artery.

7. The stent of claim 1 wherein the segments have a substantially uniform wall thickness.

8. The stent of claim 1 wherein the first and second connectors have substantially the same thickness as the segments.

9. The stent of claim 1 wherein the first and second connectors are in the same cylindrical plane as the segments.

10. The stent of claim 1 wherein each tubular shaped segment is elongated.

11. The stent of claim 1 wherein the stent is formed in a unitary structure from a continuous thin-walled tubular member.

12. The stent of claim 1 wherein the first and second connectors are elongate members.

13. A balloon expandable coronary stent for delivery to a coronary artery through an access artery, the stent comprising:

at least three segments, each segment having a generally tubular shape and a first end and a second end;

each segment having a plurality of openings that are disposed substantially parallel to the longitudinal axis of the segment, the openings forming a series of alternating open and closed portions in each of the first and second ends of the segment;

a first connector extending between and connecting a portion of a first segment to a portion of a second segment;

a second connector extending between and connecting a portion of the second segment to a portion of a third segment;

the first and second connectors being straight elongate members that are substantially parallel to the longitudinal axis of the stent and are angularly offset from each other with respect to the longitudinal axis of the stent;

whereby each of the segments may be displaced at an angle with respect to the longitudinal axis of an adjacent segment when the stent is delivered through a curved portion of the access or coronary arteries; and the stent having a first diameter which permits intraluminal delivery of the stent through the access artery by percutaneous catheterization and a second, expanded and deformed diameter, the second diameter being attained upon the application from the interior of the stent of a radially, outwardly directed force by inflating a balloon, which second diameter is variable and dependent upon the amount of force applied to the stent, whereby the stent may be expanded and deformed beyond its elastic limit to expand the lumen of the coronary artery.

14. The stent of claim 13 wherein at least one of the first and second connectors is flexible.

15. The stent of claim 13 wherein the segments may articulate about the first and second connectors.

16. The stent of claim 13 wherein the stent is formed in a unitary structure from a continuous thin-walled tubular member.

17. The stent of claim 13 wherein each of the segments include at least one cylindrical element that has alternating open and closed portions defining a wave pattern having a plurality of peaks and valleys.

18. The stent of claim 13 wherein at least one of the segments may individually function as a structure that maintains patency of the lumen of the coronary artery.

19. The stent of claim 13 wherein the segments have a substantially uniform wall thickness.

20. The stent of claim 13 wherein the first and second connectors have substantially the same thickness as the segments.

21. The stent of claim 13 wherein each tubular shaped segment is elongated.

22. A balloon expandable coronary stent for delivery to a coronary artery through an access artery, the stent comprising:

at least two segments, each segment having a generally tubular shape and a first end and a second end;

each segment having a plurality of openings that are disposed substantially parallel to the longitudinal axis of the segment, the openings forming a series of alternating open and closed portions in each of the first and second ends of the segment;

the segments being arranged so that at least one closed portion of the second end of a first segment is in longitudinal alignment with a closed portion of the first end of a second segment;

a connector extending between and connecting the aligned closed portion of the second end of the first segment to the aligned closed portion of the first end of the second segment, the connector being an elongate flexible member that extends between and is integrally formed with the aligned closed portions;

whereby each of the segments may be displaced at an angle with respect to the longitudinal axis of an adjacent segment when the stent is delivered through a curved portion of the access or coronary arteries; and the stent having a first diameter which permits intraluminal delivery of the stent through the access artery by percutaneous catheterization and a second, expanded and deformed diameter, the second diameter being attained upon the application from the interior of the stent of a radially, outwardly directed force by inflating a balloon, which second diameter is variable and dependent upon the amount of force applied to the stent, whereby the stent may be expanded and deformed beyond its elastic limit to expand the lumen of the coronary artery.

23. The stent of claim 22 wherein the segments may articulate about the connector.

24. The stent of claim 22 wherein each of the segments include at least one cylindrical element formed from a plurality of struts so as to define the open and closed portions.

25. The stent of claim 22 wherein at least one of the segments may individually function as a structure for maintaining patency of the lumen of the coronary artery.

26. The stent of claim 22 wherein the segments have a substantially uniform wall thickness.

27. The stent of claim 22 wherein the connector has substantially the same thickness as the segments.

28. The stent of claim 22 wherein the connector is in the same cylindrical plane as the segments.

29. The stent of claim 22 wherein each tubular shaped segment is elongated.

30. The stem of claim 22 wherein the stent is formed in a unitary structure from a continuous thin-waled tubular member.

* * * * *